United States Patent
Flexman et al.

(10) Patent No.: US 10,939,967 B2
(45) Date of Patent: Mar. 9, 2021

(54) ROBOTIC CONTROL OF AN ENDOVASCULAR DEPLOYMENT DEVICE WITH OPTICAL SHAPE SENSING FEEDBACK

(71) Applicant: KONINKLIJKE PHILIPS N.V., Eindhoven (NL)

(72) Inventors: Molly Lara Flexman, Melrose, MA (US); Gregory Cole, Ossining, NY (US); David Paul Noonan, New York, NY (US); Neriman Nicoletta Kahya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 67 days.

(21) Appl. No.: 15/544,547

(22) PCT Filed: Jan. 6, 2016

(86) PCT No.: PCT/IB2016/050044
§ 371 (c)(1),
(2) Date: Jul. 19, 2017

(87) PCT Pub. No.: WO2016/116821
PCT Pub. Date: Jul. 28, 2016

(65) Prior Publication Data
US 2018/0263716 A1 Sep. 20, 2018

Related U.S. Application Data

(60) Provisional application No. 62/106,262, filed on Jan. 22, 2015.

(51) Int. Cl.
*A61B 34/30* (2016.01)
*A61F 2/954* (2013.01)
(Continued)

(52) U.S. Cl.
CPC ............. *A61B 34/30* (2016.02); *A61B 6/12* (2013.01); *A61B 6/4441* (2013.01); *A61B 6/487* (2013.01);
(Continued)

(58) Field of Classification Search
CPC ......... A61B 34/30; A61B 34/35; A61B 34/37; A61B 34/70; A61B 34/71;
(Continued)

(56) References Cited

U.S. PATENT DOCUMENTS

6,665,554 B1 * 12/2003 Charles .................. A61B 90/36
600/427
6,810,281 B2 * 10/2004 Brock .................. A61B 5/7455
600/407
(Continued)

*Primary Examiner* — George J Ulsh (57) ABSTRACT

A robotic system for operating a endovascular deployment device (40) including a treatment device (43) mounted to a delivery tool (42) connected to a proximal control (41), and further including an optical shape sensor (44) (e.g., an endograft endovascular deployment device incorporating an optical shape sensor). The robotic system employs a robot (50) attachable to proximal control (41) and/or delivery tool (42) for navigating the treatment device (43) within a cardiovascular system (e.g., a robot controlling an axial rotation and/or axial translation of an endograft mounted to a sheath catheter). The robotic system further employs a robot controller (74) for controlling a navigation of treatment device (43) within the cardiovascular system by the robot (50) derived from a spatial registration between a shaping sensing by the optical shape sensor (44) of a portion or entirety of endovascular deployment device (40) to a medical image of the cardiovascular system (e.g., an X-ray/reconstructed image of an abdominal aorta).

14 Claims, 6 Drawing Sheets

(51) Int. Cl.
  *A61B 6/12* (2006.01)
  *A61B 6/00* (2006.01)
  *A61B 34/37* (2016.01)
  *A61B 34/20* (2016.01)
  *A61B 90/00* (2016.01)
  *A61B 34/00* (2016.01)

(52) U.S. Cl.
  CPC ............. *A61B 6/504* (2013.01); *A61B 6/54* (2013.01); *A61B 34/20* (2016.02); *A61B 34/37* (2016.02); *A61B 90/37* (2016.02); *A61F 2/954* (2013.01); *A61B 34/76* (2016.02); *A61B 2034/2061* (2016.02); *A61B 2034/301* (2016.02); *A61B 2090/061* (2016.02); *A61B 2090/065* (2016.02); *A61B 2090/376* (2016.02)

(58) Field of Classification Search
  CPC ........ A61B 2034/301; A61B 2034/302; A61B 2034/303; A61B 2034/305; A61B 2034/306
  See application file for complete search history.

(56) References Cited

U.S. PATENT DOCUMENTS

| | | | |
|---|---|---|---|
| 7,930,065 B2 | 4/2011 | Larkin et al. | |
| 8,460,175 B2 * | 6/2013 | Jo | A61B 1/00149 600/102 |
| 8,528,565 B2 | 9/2013 | Hauck et al. | |
| 9,259,278 B2 | 2/2016 | Jensen | |
| 9,326,788 B2 * | 5/2016 | Batross | A61B 17/320092 |
| 9,404,734 B2 | 8/2016 | Ramamurthy et al. | |
| 9,623,209 B2 | 4/2017 | Wenderow | |
| 9,726,476 B2 | 8/2017 | Ramamurthy et al. | |
| 2007/0156019 A1 | 7/2007 | Larkin et al. | |
| 2008/0188921 A1 | 8/2008 | Yamasaki | |
| 2009/0228020 A1 | 9/2009 | Wallace et al. | |
| 2011/0224686 A1 | 9/2011 | Larkin et al. | |
| 2012/0191086 A1 | 7/2012 | Moll et al. | |
| 2012/0283747 A1 | 11/2012 | Popovic | |
| 2013/0324833 A1 | 12/2013 | Barley | |
| 2014/0052241 A1 | 2/2014 | Godefridus et al. | |
| 2014/0275997 A1 | 9/2014 | Chopra et al. | |
| 2014/0316436 A1 * | 10/2014 | Bar | A61B 17/1757 606/130 |
| 2014/0343416 A1 * | 11/2014 | Panescu | A61B 34/30 600/431 |
| 2014/0343568 A1 * | 11/2014 | Fenech | A61B 34/30 606/130 |
| 2015/0045813 A1 * | 2/2015 | Kostrzewski | A61B 19/26 606/130 |
| 2015/0057575 A1 | 2/2015 | Tsusaka | |
| 2015/0141808 A1 | 5/2015 | Elhawary et al. | |
| 2015/0209112 A1 | 7/2015 | Moll et al. | |
| 2016/0081760 A1 | 3/2016 | Verard | |
| 2016/0183841 A1 * | 6/2016 | Duindam | A61B 17/34 600/424 |
| 2016/0256230 A1 * | 9/2016 | Kowshik | A61B 34/71 |
| 2017/0203116 A1 | 7/2017 | Sadler | |

* cited by examiner

ROBOTIC CONTROL OF AN ENDOVASCULAR DEPLOYMENT DEVICE WITH OPTICAL SHAPE SENSING FEEDBACK

CROSS-REFERENCE TO PRIOR APPLICATIONS

This application is the U.S. National Phase application under 35 U.S.C. § 371 of International Application Serial No. PCT/IB2016/050044, filed on Jan. 6, 2016, which claims the benefit of U.S. Application Ser. No. 62/106,262, filed on Jan. 22, 2015. These applications are hereby incorporated by reference herein.

FIELD OF THE INVENTION

The present invention generally relates to minimally invasive endovascular interventional procedures including endovascular aneurysm repair ("EVAR") and fenestrated EVAR ("FEVAR") of an abdominal aortic aneurysm ("AAA"). The present invention specifically relates to a robotic control of the endovascular interventional procedures including robotic control of a EVAR/FEVAR deployment of an endovascular stent-graft ("endograft") within the abdominal aorta to impede blood flood along the walls of the AAA.

BACKGROUND OF THE INVENTION

An aorta is a main artery of a body that carries oxygen-rich blood from a heart through the body. An abdominal aorta aneurysm ("AAA") is a bulge/ballooning in a weakened section of the aorta within an abdominal region of the body whereby the aorta may rupture and cause excessive internal bleeding within the abdomen that quickly results in death.

Figure 1A:
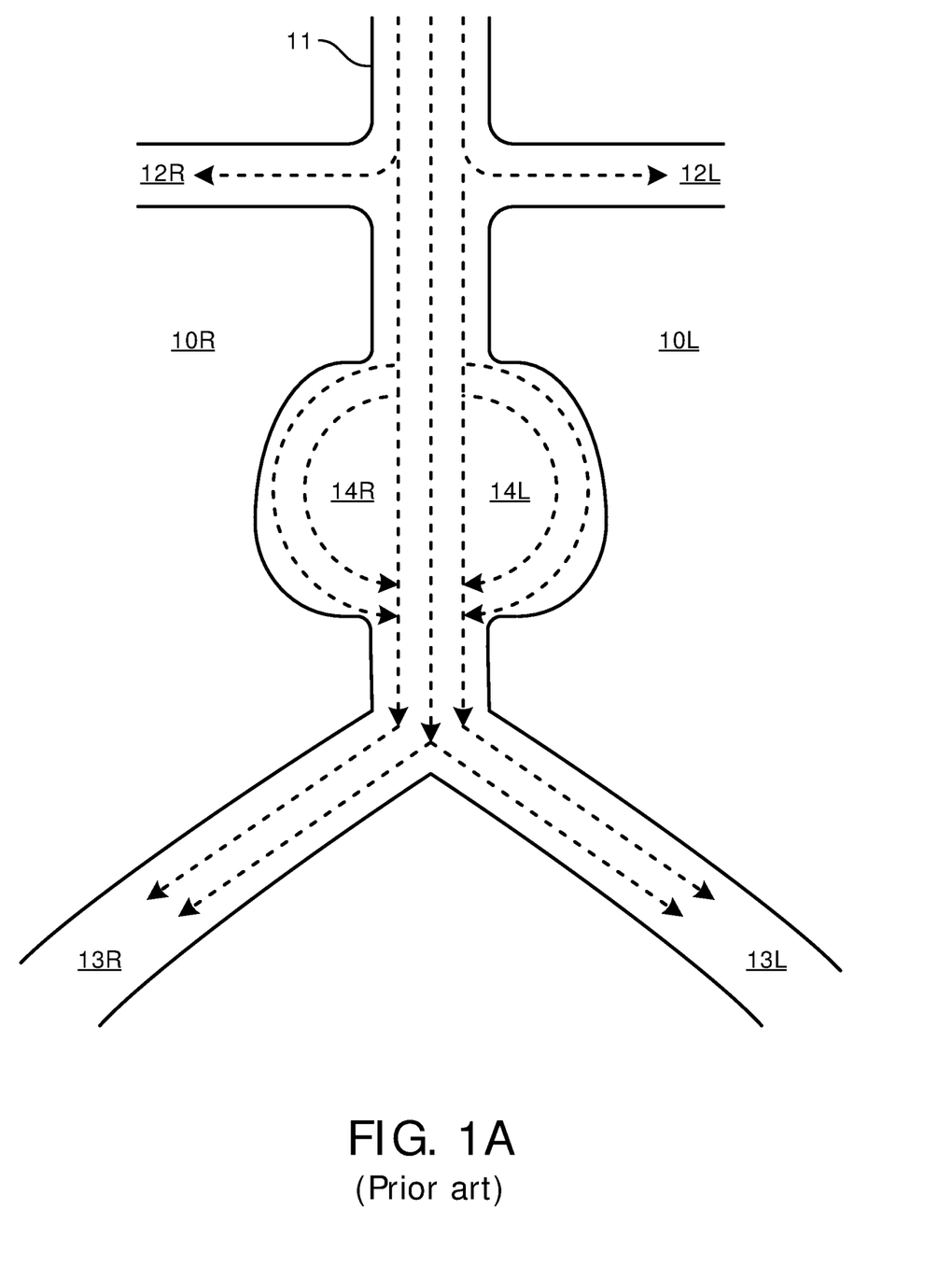
FIGS. 1A-1C illustrate an exemplary endograft deployment for repairing an abdominal aorta aneurysm as known in the art.
Figure 1B:
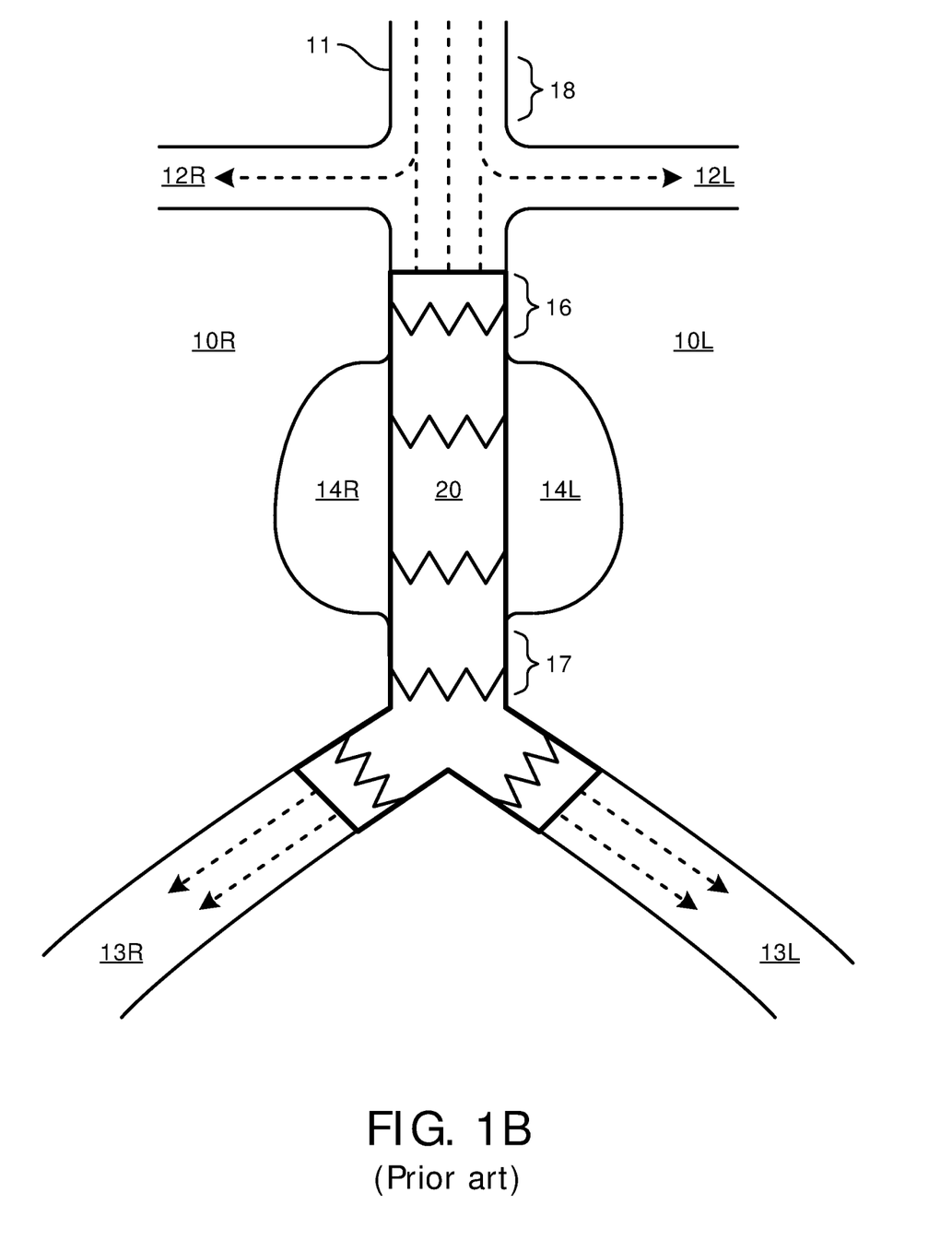
Figure 1C:
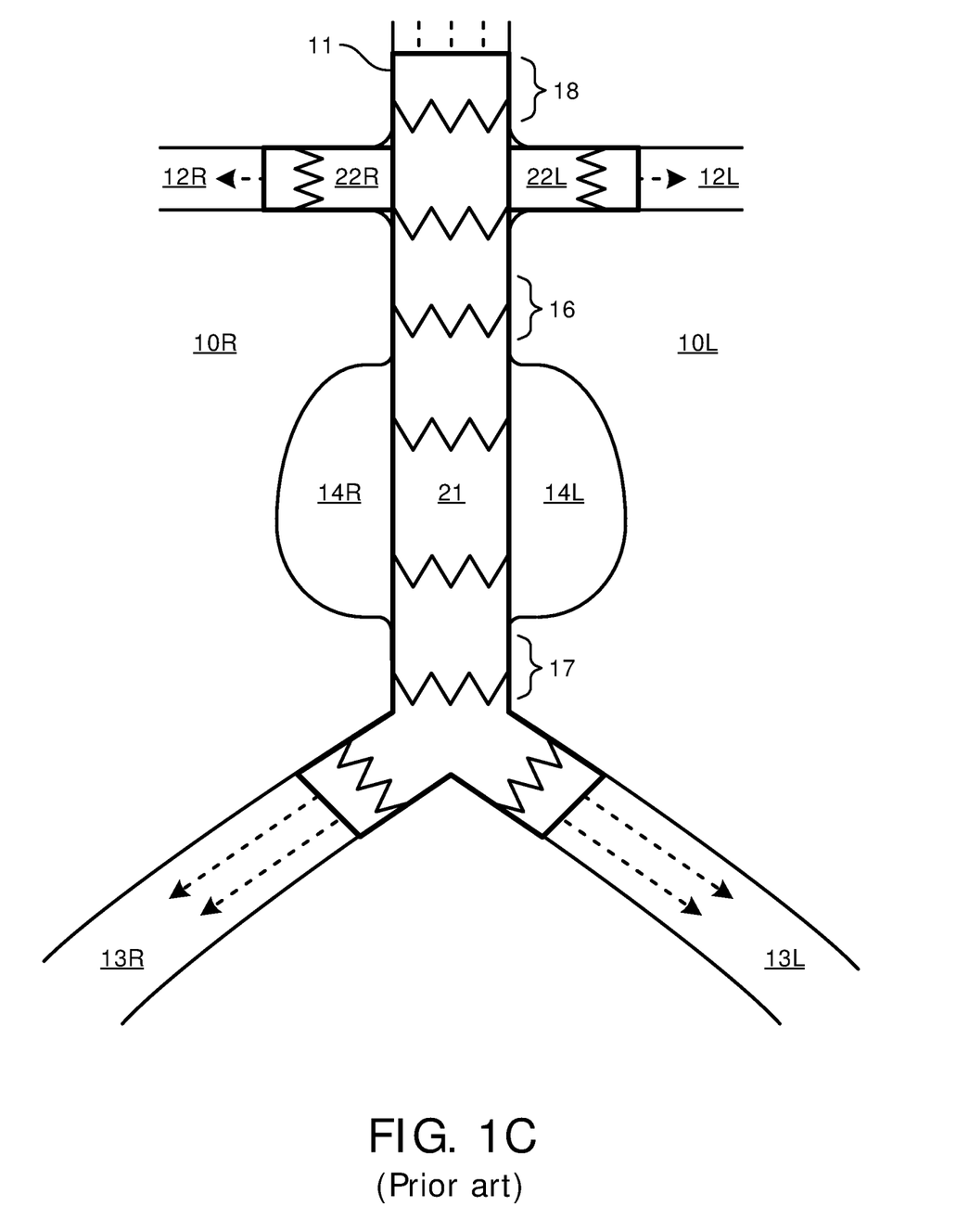

For example, FIG. 1A-C illustrates an aorta 11 within an abdomen 10R,L with including a right renal artery 12R, a left renal artery 12L, a right iliac artery 13R and a left iliac artery 13L branching from abdominal aorta 11. Shown within abdominal aorta 11 between artery branches 12 and 13 is an aneurysm 14R,L that may have been caused by various factors including high blood pressure, atherosclerosis and aging. Typical blood flow through aorta 11 to aortic branches 12 and 13 as symbolized by the dashed arrows strains the walls of aneurysm 14, which may cause aorta 11 to balloon, eventually leading to rupture, which can cause excessive internal bleeding within abdomen 10 that quickly results in death.

Various procedures have been proposed to repair AAA, of which, endovascular aneurysm repair ("EVAR") and fenestrated EVAR ("FEVAR" are currently the most common techniques for the repair of an AAA. An EVAR/FEVAR procedure is typically carried out under x-ray fluoroscopy guidance and uses significant amounts of contrast and radiation to correctly position and orient an endovascular stent-graft ("endograft") within the abdominal aorta for deploying the endograft to control the flow of blood through the AAA.

For example, FIG. 1B illustrates an endograft 20 that was deployed under x-ray fluoroscopy guidance in abdominal aorta 11 to maintain continual blood flow to aortic branches 12 and 13 while reducing pressure along the walls of aneurysm 14.

By further example, FIG. 1C illustrates a fenestrated endograft 21 with branch grafts 22 that were deployed under x-ray fluoroscopy guidance in abdominal aorta 11 to maintain continual blood flow to aortic branches 12 and 13 while impeding blood flood away along the walls of aneurysm 14.

There are various complications associated with an EVAR/FEVAR procedure.

First, on average, 50-100 mL of contrast dye is used during an EVAR/FEVAR procedure, which can result in acute renal failure in ~7% of cases.

Second, the most common complication from an EVAR/FEVAR procedure is endoleaks resulting from an insufficient seal of the endograft to the abdominal aorta whereby the endoleaks involve incorrect blood flow around the endograft into the aneurysm.

For example, referring to FIG. 1B, an endoleak may result with blood flow around an insufficient seal of endograft 20 to aorta 11 at a proximal attachment site 16 and/or at a distal attachment site 17. An endoleak may further result from blood flow through a wall of endograft 20 into aneurysm 14 or retrograde blood flow side branches.

Similarly, for example, referring to FIG. 1C, an endoleak may occur with blood flow around an insufficient seal of endograft 21 to aorta 11 at a proximal attachment site 16, and/or at a distal attachment site 17 and/or at a proximal attachment site 18. An endoleak may further result from blood flow through a wall of endograft 21 into aneurysm 14 or retrograde blood flow from aortic branches Third, another complication around EVAR/FEVAR procedures involves ischemia of the aortic side branches including the colonic, renal, and pelvic arteries. This can occur due to misplacement of the endograft such that the endograft partially or completely covers one of the side branches.

For example, referring to FIG. 1B, an attachment of endograft 20 at attachment site 18 would cover renal arteries 12, which could lead to renal artery occlusion.

More particularly to the x-ray fluoroscopy guidance for EVAR/FEVAR procedures, an endograft is contained within a deployment system that is used to navigate the endograft to a position and/or an orientation for deployment within the aorta. Such deployment systems tend to be relatively large and stiff endovascular devices. They typically involve a handle or set of knobs and dials at the proximal end of the device to control the various steps around the stent deployment at the distal end of the device. Specifically, the endograft lies within a distal part of the device and is only released once the device has been navigated to the appropriate position and/or orientation within the aorta. In some cases the endograft completely deploys in one step, while in other cases the endograft can be partially deployed to allow for correct positioning and/or orientation before the final deployment step firmly attaches the endograft to the vasculature through a retaining/sealing ring.

The endograft requires a sufficient amount of healthy vasculature whereby the retaining/sealing ring can be properly attached to the vasculature. If a healthy proximal attachment site is available beneath the renal arteries, then the endograft will not cover the renal arteries and may be attached to the vasculature below the renal arteries via a correct positioning and/or orientating of the deployment device.

For example, referring to FIG. 1B, a deployment device was manually operated via x-ray fluoroscopy guidance to navigate endograft 20 to a healthy attachment site 16 below renal arteries 12 whereby renal arteries 12 are not covered or blocked by endograft 20 upon the shown attachment of endograft 20 to aorta 11.

Conversely, if a healthy proximal attachment site is unavailable beneath the renal arteries, then alternative approaches are necessary to maintain flow to those arteries.

One approach is to use a fenestrated endograft. In this case, the fenestrations of the fenestrated endograft must be lined up correctly with renal arteries and additional stents are placed within the renal arteries to connect the renal arteries to the main endograft.

For example, referring to FIG. 1C, a deployment device proper was manually operated via x-ray fluoroscopy guidance to navigate main endograft 21 to a healthy attachment site 18 above renal arteries 12 and to align the fenestrations of main endograft 21 with renal arteries 12 whereby additional endografts 22R,L were placed within renal arteries 12.

Under the x-ray fluoroscopy guidance, the endograft is visualized through x-ray visible markers that are located in key positions on the endograft including the retaining/sealing ring(s) and fenestrations, if any. Nonetheless, there are several drawbacks to a manual operation of the deployment device under x-ray fluoroscopy guidance including an inherent degree of difficulty in achieving a precise positioning and orientation of an endograft, a practical degree of instability of the endograft during the deployment (particularly for extension and cannulation of the aortic side branches), and lack of an intuitive concurrent control of the endograft and the c-arm of the x-ray device.

SUMMARY OF THE INVENTION

Endovascular surgery as known in the art generally is a minimal invasive intervention involving access through major blood vessels to a targeted area of a cardiovascular system including a heart and all blood vessels. Examples of endovascular surgery include, but are not limited to, EVAR, FEVAR, coronary stenting, peripheral vascular ballooning and stenting, mitral valve replacement, mitral clip placement, aortic valve replacement, left atrial appendage closure, perivalvular leak closure, etc.

The present invention proposes a novel and unique integration of optical shape sensing and robotic control for navigating a treatment device within the cardiovascular system, more particularly a novel and unique integration of optical shape sensing with robotic control for navigating an endograft within an abdominal aorta during an EVAR or FEVAR.

One form of the present invention is a robotic system for operating an endovascular deployment device including a treatment device mounted to a delivery tool connected to a proximal control, and further including an optical shape sensor (e.g., an endograft deployment device incorporating an optical shape sensor). The robotic system employs a robot attachable to the proximal control and/or the delivery tool for navigating the treatment device within a cardiovascular system (e.g., a robot controlling an axial rotation and/or axial translation of an endograft mounted to a sheath catheter within an abdominal aorta). The robotic system further employs a robot controller for controlling a navigation of the treatment device within the cardiovascular system by the robot derived from a spatial registration between a shaping sensing of a portion or entirety of the endovascular deployment device by the optical shape sensor and a medical image of the cardiovascular system (e.g., a spatial registration of shape sensing data to an X-ray/reconstructed image of an abdominal aorta).

For purposes of the present invention, the terms of the art of the present invention including, but not limited to "optical shape sensor", "endograft", "deployment device", "robot", "navigating/navigation", "control/controlling", "spatial registration", "shape sensing" and "cardiovascular system" are to be interpreted as understood in the art of the present invention and as exemplary described herein.

For purposes of the present invention, the term "endovascular deployment device" broadly encompasses and descriptively labels all known deployment devices for deploying endotreatment device including, but not limited to, the Endurant®II AAA Stent Graft System, the Zenith® System for AAA, the AFX® Endovascular AAA System, MitraClip Percutaneous Mitral Valve Repair System, WATCHMAN Left Atrial Appendage Closure Device, SAPIEN XT Transcatheter Heart Valve, and in general endograft, stent, clip, and valve delivery and deployment systems.

For purposes of the present invention, the term "proximal control" broadly encompasses and descriptively labels deployment controls located at a proximal end of known endovascular deployment devices including, but not limited to, knobs, wheels, screws, injection channels, pull wires, sliders, levers etc.

For purposes of the present invention, the term "delivery tool" broadly encompasses and descriptively labels tools distally extending from the proximal control for mounting treatment device including, but not limited to, deployment devices, sheath catheters, balloon catheters, guidewires, etc.

For purposes of the present invention, the term "treatment device" broadly encompasses and descriptively labels tools distally extending from the proximal control and for mounting treatment device including, but not limited to, endografts (non-fenestrated and fenestrated), stents, clips, valves, closure devices, annuloplasty rings, etc.

For purposes of the present invention, the term "medical image" broadly encompasses all known image forms utilized for diagnosis, planning and guidance of vascular interventional procedures including, but not limited to, modality images (e.g., an X-ray image), reconstructed images, rendered images, segmented images, modeled images, etc.

For purposes of the present invention, the term "controller" broadly encompasses all structural configurations of an application specific main board or an application specific integrated circuit housed within or linked to a computer or another instruction execution device/system for controlling an application of various inventive principles of the present invention as subsequently described herein. The structural configuration of the controller may include, but is not limited to, processor(s), computer-usable/computer readable storage medium(s), an operating system, application module(s), peripheral device controller(s), slot(s) and port(s). Examples of a computer includes, but is not limited to, a server computer, a client computer, a workstation and a tablet.

For purposes of the present invention, the term "module" broadly encompasses a component of the imaging quality controller consisting of an electronic circuit or an executable program (e.g., executable software and/or firmware) for executing a specific application.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

To facilitate an understanding of the present invention, an example of a system for executing an EVAR procedure and a FEVAR procedure will now be described in connection with FIGS. 2-6. From the description of FIGS. 2-6, those having ordinary skill in the art will understand how to make and use the present invention for additional types of endovascular interventional procedures in accordance with the inventive principles of the present invention including, but not limited to, endovascular interventional procedures for the peripheral vasculature, thoracic aorta, as well as transcatheter cardiac procedures.

For purposes of the present invention, the terms of the art of the present invention including, but not limited to "optical shape sensor", "sheath catheter", "guidewire", "catheter balloon", "monitor", "interface" and "workstation" are to be interpreted as known in the art of the present invention and exemplary described herein.

Figure 2:
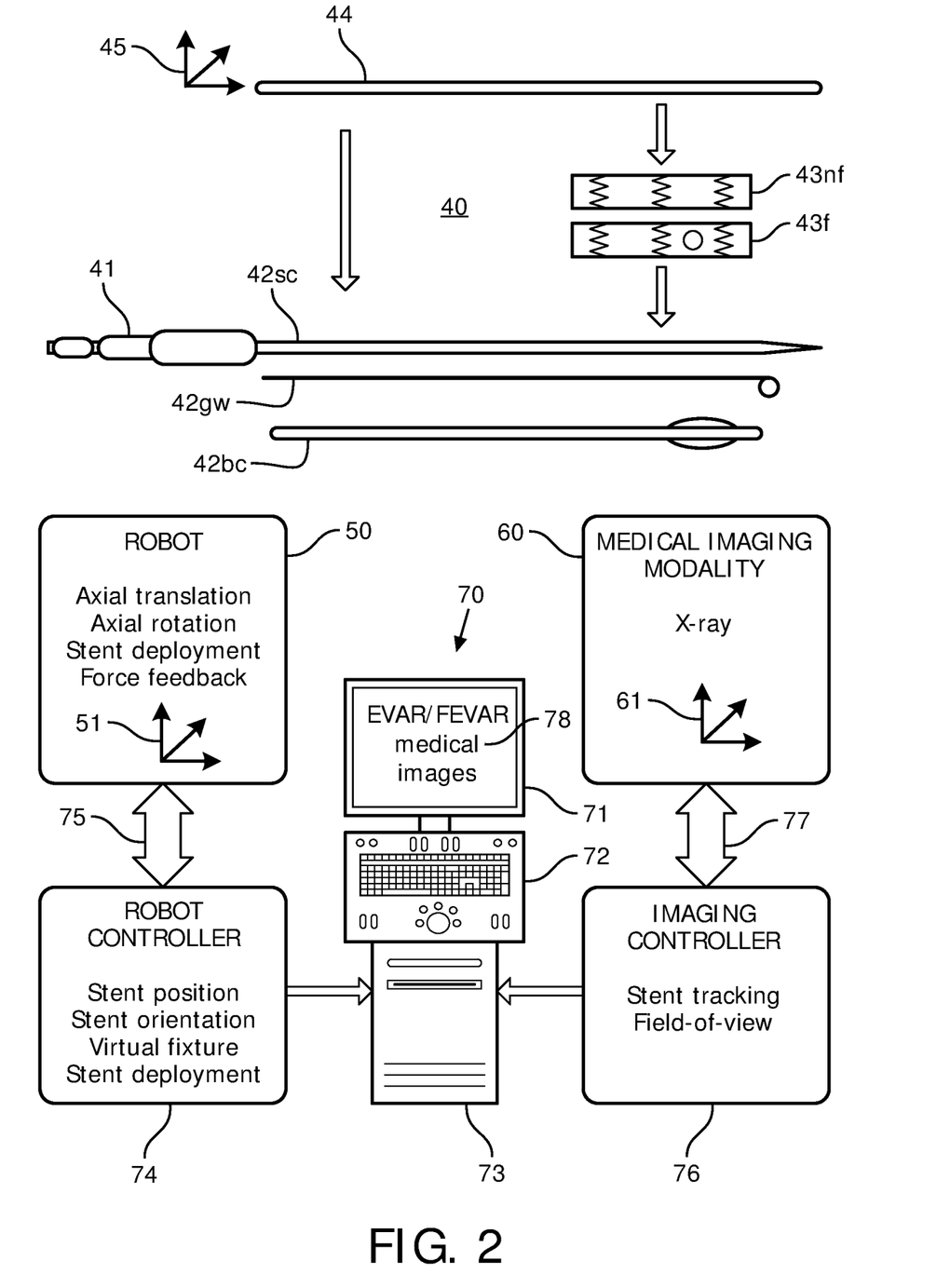
FIG. 2 illustrates an exemplary embodiment of a robotic endograft deployment system in accordance with the inventive principles of the present invention.

Referring to FIG. 2, an EVAR/FEVAR system of the present invention employs:
(1) an endograft deployment device 40 including
  (a) a proximal control 41,
  (b) delivery tools in the form of a sheath catheter 42sc, a guidewire 42gw, and/or a balloon catheter 42bc,
  (c) treatment device the form of a non-fenestrated endograft 43nf or a fenestrated endograft 43f, and
  (d) one or more optical shape sensors 44; and
(2) a robot (50);
(3) a medical imaging modality 60;
(4) a robot control workstation 70.

Optical shape sensor ("OSS") 44 uses light along one or more optical fibers for device localization and navigation during the EVAR/FEVAR procedure. An operating principle of OSS sensor 30 involves use of distributed strain measurement in the optical fiber including, but not limited to, use of characteristic Rayleigh backscatter or use of controlled grating patterns. A shape along the optical fiber begins at a specific point along OSS 44 associated with an origin of a OSS coordinate system 45 whereby a subsequent shape position and orientation of OSS 44 are relative to the origin of OSS coordinate system 45.

In order to introduce the use of OSS 44 into the EVAR/FEVAR procedure for providing image guidance of endograft 43nf or fenestrated endograft 43f, in practice OSS 44 may integrated into the endograft development in accordance with various approaches including, but not limited to:
(1) an integration of OSS 44 into endograft 43nf or fenestrated endograft 43f;
(2) discrete points of attachment of OSS 44 onto endograft 43nf or fenestrated endograft 43f;
(3) integration of OSS 44 into a wall of catheters 42sc and 42bc;
(4) attachment of OSS 44 to a handle of proximal control 41; and
(5) integration of OSS 44 into the guidewire 42gw.

"As further described herein, medical imaging such as image rendering and image modeling of endograft 43nf or fenestrated endograft 43f may be generated based on the optical shape sensing information in dependence upon the integration method. Robot 50 is attached to proximal control 41 and/or a delivery tool (e.g., heath catheter 42sc, guidewire 42gw and balloon catheter 42bc), for navigating endograft 43nf or fenestrated endograft 43f within an abdominal aorta. In practice, an attachment of robot 50 to proximal control 41 and/or the delivery tool includes, but is not limited to:
(1) a clamping of robot onto a torsional component of endograft deployment device 40 coupled to delivery tool (e.g., a handle of proximal control 41);
(2) a use of a mating piece between endograft deployment device 40 and robot 50; and
(3) a passing of sheath catheter 42sc through a collet attached to robot 50."

Figure 3:
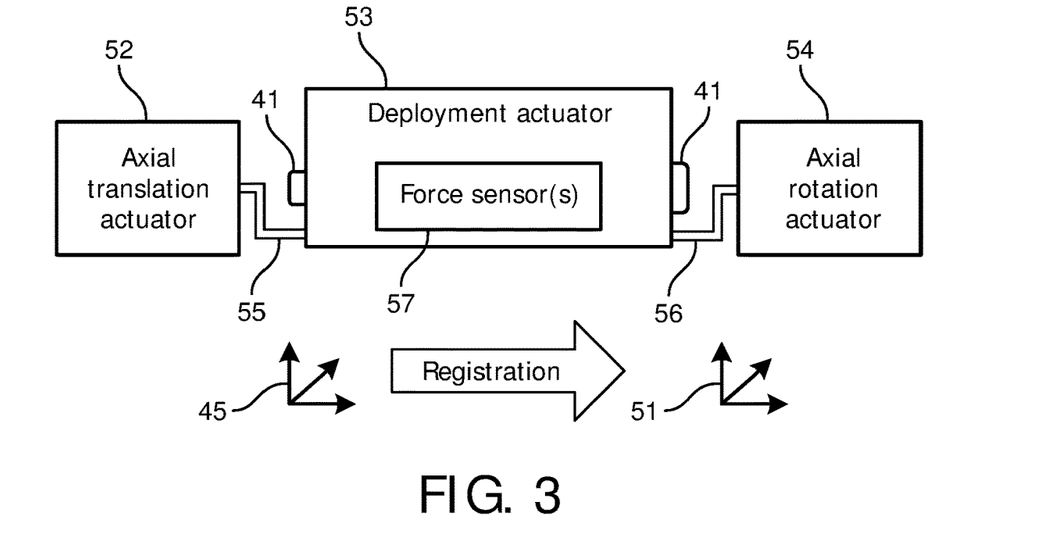
FIG. 3 illustrates an exemplary embodiment of a robot in accordance with the inventive principles of the present invention.

In one embodiment of robot 50 (FIG. 2, 4) as shown in FIG. 3, a deployment actuator 53 clamps down on a handle of proximal control 41 whereby an axial translation actuator 52 may axially translate the delivery tools (not shown) via a translatable gear 55 as commanded by robot control workstation 70 for endograft position purposes, and whereby the deployment actuator 53 may axially rotate the delivery tools (not shown) via a rotatable gear 56 as commanded by robot control workstation 70 for endograft orientation purposes. For this embodiment, OSS coordinate system 45 may be spatially registered to a robot coordinate system 51 or vice-versa.

A key feature of robot 50 is the ability to hold endograft deployment device 40 and therefore endograft 43nf/fenestrated endograft 43f in a stable position/orientation that reduces a need for an operator to be holding a handle of proximal control in position/orientation at all times. In the event that endograft deployment device 40 and therefore endograft 43nf/fenestrated endograft 43f does slip, robot 50 may automatically attempt to reposition/reorient endograft 43nf/fenestrated endograft 43f within the abdominal aorta 11 or can warn the user. In addition, by incorporating force sensor(s) 57 as shown, forces required to insert endograft deployment device 40 into the abdominal aorta may be measured and force(s) required to hold endograft 43nf/fenestrated endograft 43f during vessel cannulation, etc., may also be measured. Such force readings could be used to warn the operator if excessive forces were applied to the patient.

Figure 4:
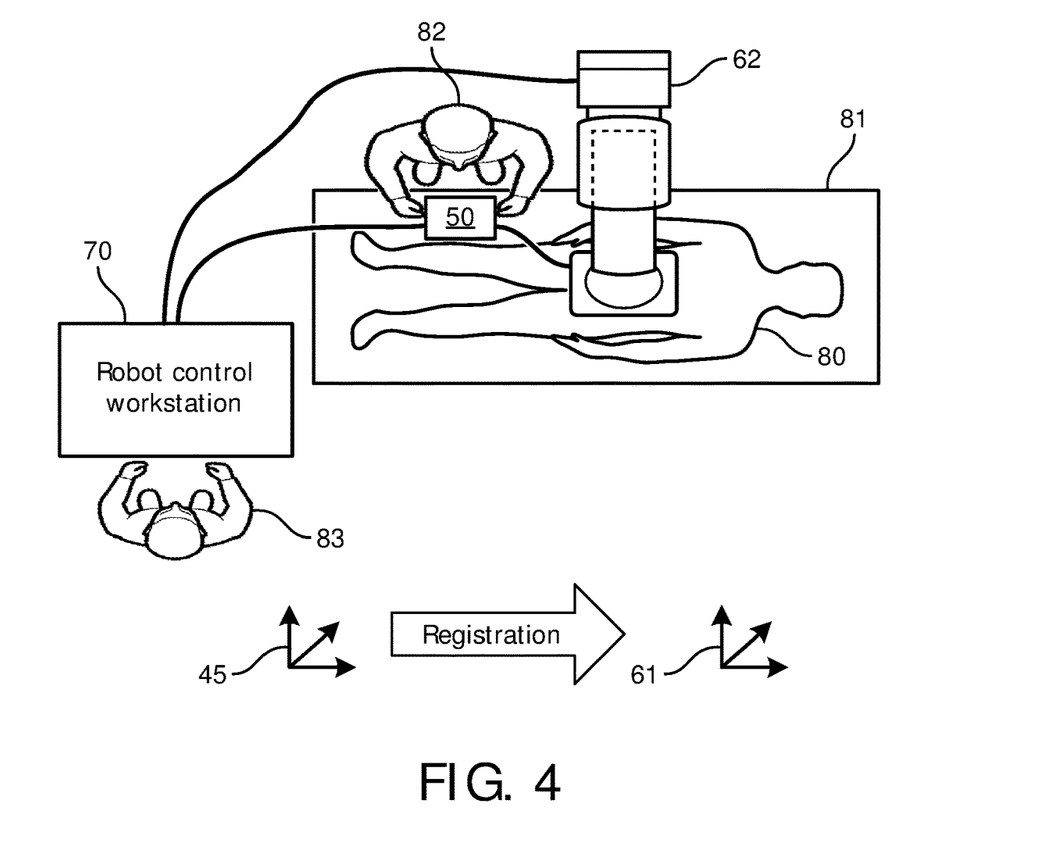
FIG. 4 illustrates an exemplary control of an x-ray system in accordance with the inventive principles of the present invention.

Referring back to FIG. 2, medical imaging modality 60 may be any known imaging modality as known in the art including. Preferably, as shown in FIG. 4, imaging modality 60 is an X-ray machine having a C-arm positioned and oriented for imaging the abdominal aorta of a patient 80. For the imaging, OSS coordinate system 45 is spatially registered with an image coordinate system 61 or to landmarks/targets identifiable in X-ray images whereby the shape sensing data of OSS 30 is spatially registered to any medical image generated from the X-ray imaging for robotic control purposes. In practice, OSS coordinate system 45 may be spatially registered to image coordinate system 61 or vice-versa, and OSS coordinate system 45 may be spatially registered to the landmarks/targets or vice-versa.

Of importance to note is the integration of OSS 44 and robot 50 into the EVAR/FEVAR procedure reduces X-ray exposure for a robot monitor and a workstation operator.

Referring back to FIG. 2, robot control workstation 70 employs a monitor 71, an interface platform 72, a interface platform 73, a robot controller 74 installed within interface platform 73 and an imaging controller 76 installed within interface platform 73.

Interface platform 73 is connected/coupled to OSS 44 and imaging modality 60 to respectively input shape sensing data and imaging data. More particularly, for the input of shape sensing data, a light detector (not shown) as known in the art for detecting light reflected by and/or transmitted through OSS 44 may be internal or external to interface platform 73.

Robot controller 74 and imaging controller 76 include and/or are accessible by an operating system (not shown) as known in the art for controlling various graphical user interfaces, data and images on monitor 78 as directed by a workstation operator via a keyboard, buttons, dials, joysticks, etc. of interface platform 72, and for storing/reading data as programmed and/or directed by the workstation operator of interface platform 72.

In practice, robot controller 74 and imaging controller 76 may be segregated or integrated within interface platform 73, or installed on workstation computers of different robot control workstation 70. Additionally, robot controller 74 may be incorporated within robot 50 and/or imaging controller 76 may be incorporated within imaging modality 60 whereby interface platform 73 provides user interfaces for accessing robot controller 74 and/or imaging controller 76.

Generally, robot controller 74 is connected to actuator controls of robot 50 for data/command communication 75 between robot 50 and robot controller 74 including, but not limited to, actuation commands from robot controller 74 to robot 50 and actuation data from robot 50 to robot controller 74 (e.g., a degree of axial translation and/or axial rotation of endograft deployment device 40 and any force feedback). Concurrently, imaging controller 76 is connected to imaging modality 60 for data/command communication 77 between imaging modality 60 and imaging controller 76 including, but not limited to, imaging data from imaging modality 60 to imaging controller 76 and actuation commands from imaging controller 76 to imaging modality 60.

Specifically, robot controller 74 execute various control schemes for the positioning, orientation and deployment of endograft 43$nf$/fenestrated endograft 43$f$ into the abdominal aorta, and imaging controller 76 executes a control scheme for automatic control of an imaging of the abdominal aorta by imaging modality 60.

To this end, from the imaging data generated by imaging modality 60, imaging controller 76 generates EVAR/FEVAR medical image(s) 78 for display on monitor 71 including, but not limited to, a pre-operative or intra-operative image of the anatomy (such as an x-ray, CT, MRI, IVUS, OCT, or ultrasound) and an image model of endograft 43$nf$/fenestrated endograft 43$f$ and the utilized delivery tools (e.g., sheath catheter 42$sc$, guidewire 42$gw$ and balloon catheter 42$bc$). From image(s) 78, the workstation operator implements the control schemes via interface platform 72.

Figure 5:
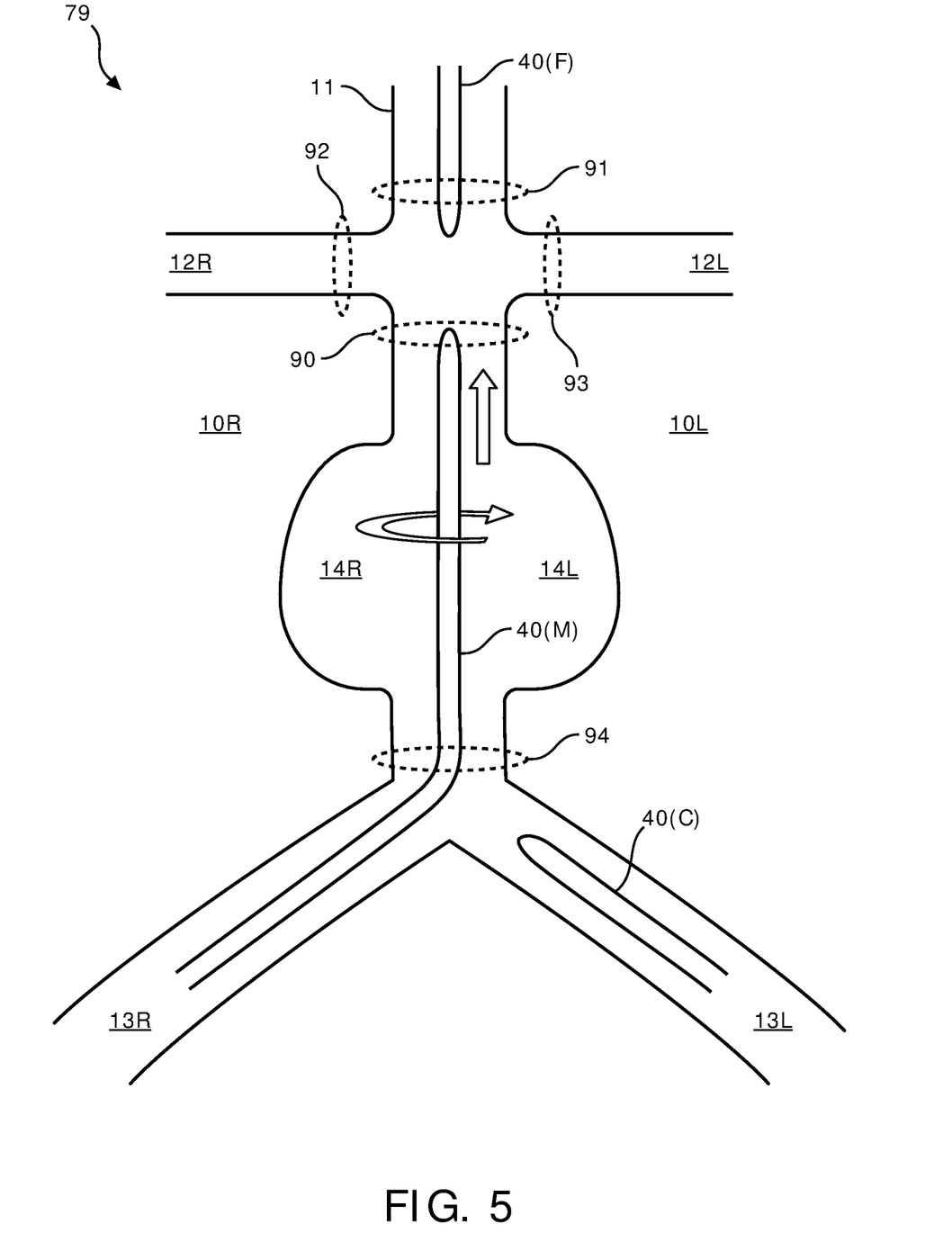
FIG. 5 illustrates an exemplary image of endograft deployment for repairing an abdominal aorta aneurysm in accordance with the inventive principles of the present invention.

The control schemes will now be described herein in the context of a two-dimensional ("2D") medical image 79 as shown in FIG. 5 of a pre-deployment insertion of a main endograft deployment device 40(M), a cannulation endograft deployment device 40(C) and a fenestration endograft deployment device 40(F) within abdominal aorta 11.

For purposes of the present invention, the terms "delivery position target" and "delivery orientation target" respectively broadly encompass a navigation target within the cardiovascular system of a position and an orientation of a specific feature of a delivery tool or a treatment device prior to or during deployment, and the terms "delivery position restriction" and "delivery orientation restriction" respectively broadly encompass a navigation boundary within the cardiovascular system of a position and an orientation of a specific feature of a delivery tool or a treatment device prior to or during deployment.

The following control schemes will be described in terms of "an endograft position target" and "an endograft orientation target" respectively broadly encompassing a navigation target within an abdominal aorta of a position and an orientation of a sealing/retaining ring of an endograft prior to deployment, and the terms "sheath position restriction" respectively broadly encompass a navigation boundary within an abdominal aorta of a position a sheath catheter during the deployment.

From this description of the control schemes, those having ordinary skill in the art will appreciate how to implement variations of the described control schemes in accordance with the inventive principles of the present invention.

Robotic Position Control Scheme. For this control scheme, robot controller 74 controls a position of endograft 43$nf$/fenestrated endograft 43$f$ by using the optical shape sensing information about key features of endograft 43$nf$/fenestrated endograft 43$f$ and endograft deployment device 40 registered to the imaging of the abdominal aorta. More particularly, robot controller 74 determines how to command robot 50 to translate endograft 43$nf$/fenestrated endograft 43$f$ (e.g., via axial translation) by using:

(1) an endograft position target of endograft 43$nf$/fenestrated endograft 43$f$ delineated by the workstation operator via interface platform 73 within two (2) 2D fluoroscopy images (e.g. AP and LAO30) or a three-dimensional ("3D") image reconstruction of the abdominal aorta generated by imaging controller 76;

(2) a programmed amount of axial translation by the workstation operator via interface platform 73;

(3) a translational interaction by the workstation operator via interface platform 73 of an endograft model over an image reconstruction or rendering of the abdominal aorta; and (4) a direct translation control of the translation of endograft 43$nf$/fenestrated endograft 43$f$ through a user input device of interface platform 73 (e.g., a joystick).

For example, referring to FIG. 5, an endograft position target 90 below renal arteries 12 for an optically sensed sealing/retaining ring (not shown) of endograft 43$nf$ adjacent the distal tip of main endograft deployment device 40(M) may be delineated by the workstation operator via interface platform 73. In response to actuation commands from robot controller 74 associated with the delineation of endograft position target 90, robot 50 will axially translate main endograft deployment device 40(M) until the optical shape sensing feedback indicates the sealing/retaining ring is located at endograft position target 90.

Alternatively for embodiments involving the creation of fenestrations in endograft 43$nf$ during or subsequent to the deployment of endograft 43$nf$, an endograft position target 91 above renal arteries 12 for an optically sensed sealing/retaining ring (not shown) of endograft 43nf adjacent the distal tip of main endograft deployment device 40(M) may be delineated by the workstation operator via interface platform 73. In response to actuation commands from robot controller 74 associated with the delineation of endograft position target 91, robot 50 will axially translate main endograft deployment device 40(M) until the optical shape sensing feedback indicates the sealing/retaining ring is located at endograft position target 91.

By further example, still referring to FIG. 5, a translational interaction or a direct translation control of main endograft deployment device 40(M) as symbolized by the one-directional linear arrow may be utilized to position an optically sensed sealing/retaining ring (not shown) of an endograft 43nf below or above renal arteries 12 as desired. In response to actuation commands from robot controller 74 associated with the translational interaction or the direct translation control, robot 50 will axially translate main endograft deployment device 40(M) until the optical shape sensing feedback indicates the sealing/retaining ring has been correspondingly translated.

This control scheme may be used for the introduction of devices 40 as shown in FIG. 5 and for fine positioning of endograft 43nf/fenestrated endograft 43f during deployment. During this control scheme, robot controller 74 may control via control the force applied by robot 50 by using the optical shape sensing information as feedback. The optical shape sensing information also provides information necessary to detect kinking or potentially dangerous curvature of device(s) 40 that could damage endograft 43nf/fenestrated endograft 43f and/or damage devices 40, for which case robot controller 74 warning could sound a warning.

Robotic Orientation Control Scheme. For this control scheme, robot controller 74 controls the orientation endograft 43nf/fenestrated endograft 43f by using the optical shape sensing information about key features of endograft 43nf/fenestrated endograft 43f registered to the imaging of the abdominal aorta. More particularly, robot controller 74 determines how to command robot 50 to orient endograft 43nf/fenestrated endograft 43f (e.g., via axial rotation) by using:

(1) an endograft orientation target of endograft 43nf/fenestrated endograft 43f delineated by the workstation operator via interface platform 73 within two (2) 2D fluoroscopy images (e.g. AP and LAO30) or 3D image reconstruction of the abdominal aorta generated by imaging controller 76;
(2) a programmed amount of axial rotation by the workstation operator via interface platform 73;
(3) a rotational interaction by the workstation operator via interface platform 73 of an endograft model over an image reconstruction or rendering of the abdominal aorta; and
(4) a direct rotation control of the translation of endograft 43nf/fenestrated endograft 43f through a user input device of interface platform 73 (e.g., a joystick).

For example, referring to FIG. 5, an endograft orientation target 92 for renal artery 12R or an endograft orientation target 93 for renal artery 12L for an optically sensed fenestration of fenestrated endograft 43f may be delineated by the workstation operator via interface platform 73. In response to actuation commands from robot controller 74 associated with the delineation of endograft orientation target 92 or endograft orientation target 93, robot 50 will axially rotate main endograft deployment device 40(M) until the optical shape sensing feedback indicates the optically sensed fenestration is orientated with endograft position target 92 or endograft orientation target 93.

By further example, still referring to FIG. 5, a rotational interaction or a direct rotation control of main endograft deployment device 40(M) as symbolized by the one-directional angular arrow may be utilized to orient an optically sensed fenestration (not shown) of fenestrated endograft 43f. In response to actuation commands from robot controller 74 associated with the rotational interaction or the direct rotation control, robot 50 will axially rotate main endograft deployment device 40(M) until the optical shape sensing feedback indicates the fenestration has been correspondingly oriented.

Endograft Deployment Control Scheme. For this control scheme, robot controller 74 communicates actuation commands to robot 50 for robotic control of the deployment of endograft 43nf/fenestrated endograft 43f.

For example with endograft deployment device 40 of FIG. 2 being a Endurant®II AAA Stent Graft System, robot 50 actuates a lead screw of proximal control 41 for the withdrawal of catheter sheath 42sc of endograft deployment device 40.

By additional example with endograft deployment device 40 of FIG. 2 being the Zenith® System for AAA, robot 50 actuates proximal control 40 to pull a wrapped thread around endograft 43nf/fenestrated endograft 43f.

Finally, by further example with endograft deployment device 40 of FIG. 2 being the AFX® Endovascular AAA System, robot 50 actuates an injection of the saline and/or polymer into endobags of proximal control 41 to ensure that the appropriate pressure is maintained.

During any such robotic actuation of the stent deployment process, information regarding a phase of the endograft deployment from actuators/encoders of robot 50 and regarding a shape of endograft deployment device 40 from OSS 44 may be used to provide the workstation operator with a virtual representation of how endograft 43nf/fenestrated endograft 43f is deploying within the visualization framework.

Virtual Fixture Control Scheme. For this control scheme, virtual boundaries for motions of the endograft deployment device may be defined within the patient anatomy or robot space. For example, as shown in FIG. 5, a endograft orientation target 93, here a sheath position restriction, depicts a virtual boundary of the sheath withdrawal of main endograft deployment device 40(M) to allow for cannulation of the contralateral artery limb 13L.

To this end, the robotic system may apply a force feedback to prevent the workstation operator from pushing the endograft deployment device into an undesired location. This "force feedback" can be expressed as a resistive force, physically limiting the workstation operator from moving the endograft deployment device into the unwanted area, or simply as a signal to the workstation operator. In practice, such a system would not require active degrees of freedom, but could be operated with resistive degrees of freedom only, which may be considered less intrusive to the workstation operator than a robotic capable of active motion. Virtual fixturing may be further used, for example, to prevent the workstation operator from blocking the renal bifurcation during the endograft deployment by limiting the depth of insertion.

Automatic Imaging Control. For this control scheme, referring to FIGS. 2 and 4, imaging controller 76 has knowledge of a position and an orientation of endograft 43nf/fenestrated endograft 43f from the optical shape sensing data and uses the knowledge to control the C-arm of the X-ray including, but not limited to:
(1) moving or suggesting an optimal position for C-arm 62 to visualize a specific feature endograft 43*nf*/fenestrated endograft 43*f* (e.g., during cannulation of a certain fenestration, workstation operator 83 may direct imaging controller 76 to move C-arm 62 to follow a translation, a rotation and/or a deployment of endograft 43*nf*/fenestrated endograft 43*f* or endograft deployment device 40);
(2) adjusting the wedges to limit the field-of-view to where endograft 43*nf*/fenestrated endograft 43*f* resides to thereby limit the radiation dose to a patient 81 and a robot operator 82; and
(3) moving a table 81 to automatically track the position of the endograft or deployment system.

In summary, referring to FIGS. 2-6, the present invention proposes a novel and unique integration of optical shape sensing and robotic control for navigating a treatment device within a vasculature of a heart, more particularly a novel and unique integration of an optical shape sensing and robotic control for navigating an endograft within an abdominal aorta.

From the description of the exemplary embodiments herein as shown in FIG. 2-6, those having ordinary skill in the art will appreciate numerous benefits of the present invention including, but not limited to:
(1) a reduction in radiation dose and use of contrast associated with imaging;
(2) stabilization and holding of the endograft deployment device;
(3) position and orientation control of the endograft deployment device; and
(4) automatic or suggested positioning of a C-arm of an X-ray system to follow relevant features of the endograft (e.g., fenestrations).

Furthermore, as one having ordinary skill in the art will appreciate in view of the teachings provided herein, features, elements, components, etc. described in the present disclosure/specification and/or depicted in the FIGS. 2-6 may be implemented in various combinations of electronic components/circuitry, hardware, executable software and executable firmware, particularly as application modules of a robot controller and imaging controller as described herein, and provide functions which may be combined in a single element or multiple elements. For example, the functions of the various features, elements, components, etc. shown/illustrated/depicted in the FIGS. 1-6 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method for robotic control of optical shape sensing based endograft deployment, (which embodiments are intended to be illustrative and not limiting), it is noted that modifications and variations can be made by persons having ordinary skill in the art in light of the teachings provided herein, including the FIGS. 2-6. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A robotic system, comprising:
   an endovascular deployment device comprising a treatment device mounted to a delivery tool connected to a proximal control, the endovascular deployment device further comprising an optical shape sensor;
   a robot attached to the proximal control and to the delivery tool to navigate the treatment device within a cardiovascular system; and
   a robot controller in communication with the robot to control a navigation of the treatment device within the cardiovascular system by the robot, wherein the robot controller is configured to derive the control of the navigation of the treatment device within the cardiovascular system by the robot from a spatial registration between a shaping sensing by the optical shape sensor of at least a portion of the treatment device and a medical image of the cardiovascular system.

2. The robotic system of claim 1,
   wherein the robot controller is configured to control the navigation of the treatment device within the cardiovascular system responsive to a delineation within the medical image of the cardiovascular system of at least one of a delivery position target for the treatment device within the cardiovascular system and a delivery orientation target for the treatment device within the cardiovascular system.

3. The robotic system of claim 1,
   wherein the robot controller is configured to control the navigation of the treatment device within the cardiovascular system responsive to a delineation within the medical image of the cardiovascular system of at least one of an axial translation of the treatment device within the cardiovascular system and an axial rotation of the treatment device within the cardiovascular system.

4. The robotic system of claim 1,
   wherein the robot controller is configured to control the navigation of the treatment device within the cardiovascular system responsive to an interaction within the medical image of the cardiovascular system of at least one of a delivery tool model illustrated within the medical image and a treatment device model illustrated within the medical image.

5. The robotic system of claim 1,
   wherein the robot controller is configured to control the navigation of the treatment device within the cardiovascular system responsive to a delineation within the medical image of the cardiovascular system of at least one of a delivery position restriction for the treatment device within the cardiovascular system and a delivery orientation restriction for the treatment device within the cardiovascular system.

6. The robotic system of claim 1,
   wherein the robot is further attached to the proximal control to deploy the treatment device within the cardiovascular system.

7. The robotic system of claim 1,
   wherein the robot is further attached to at least one of the proximal control and the delivery tool to ascertain at least one force applied by the robot to the delivery tool to thereby navigate or maintain a position of the treatment device within the cardiovascular system.

8. The robotic system of claim 1, further comprising:
   an imaging controller configured to control a generation of the medical image of the cardiovascular system by an imaging modality.

9. The robotic system of claim 8,
   wherein the robot controller is configured to control the navigation of the treatment device within the cardiovascular system responsive to a delineation within the medical image of the cardiovascular system of at least one of a delivery position target for the treatment device within the cardiovascular system and a delivery orientation target for the treatment device within the cardiovascular system.

10. The robotic system of claim 8,
    wherein the robot controller is configured to control the navigation of the treatment device within the cardiovascular system responsive to a delineation within the medical image of the cardiovascular system of at least one of an axial translation of the treatment device within the cardiovascular system and an axial rotation of the treatment device within the cardiovascular system.

11. The robotic system of claim 8,
    wherein the robot controller is configured to control the navigation of the treatment device within the cardiovascular system responsive to an interaction within the medical image of the cardiovascular system of at least one of a delivery tool model illustrated within the medical image and a treatment device model illustrated within the medical image.

12. The robotic system of claim 8,
    wherein the robot controller is configured to control the navigation of the treatment device within the cardiovascular system responsive to a delineation within the medical image of the cardiovascular system of at least one of a delivery position restriction for the treatment device within the cardiovascular system and a delivery orientation restriction of the treatment device within the cardiovascular system.

13. The robotic system of claim 8,
    wherein the robot is further attached to the proximal control to deploy the treatment device within the cardiovascular system.

14. The robotic system of claim 8,
    wherein the robot is further attached to at least one of the proximal control and the delivery tool to ascertain at least one force applied by the robot to the delivery tool to thereby navigate the treatment device within the cardiovascular system.

* * * * *